United States Patent [19]

Manzara et al.

[11] Patent Number: 5,164,521

[45] Date of Patent: Nov. 17, 1992

[54] PRIMARY HYDROXYL-TERMINATED POLYGLYCIDYL AZIDE

[75] Inventors: Anthony P. Manzara; Birger Johannessen, both of St. Paul, Minn.

[73] Assignee: Minnesota Mining and Manufacturing Company, St. Paul, Minn.

[21] Appl. No.: 780,419

[22] Filed: Oct. 22, 1991

Related U.S. Application Data

[60] Continuation of Ser. No. 361,945, Jun. 5, 1989, abandoned, which is a division of Ser. No. 771,253, Aug. 30, 1985, abandoned.

[51] Int. Cl.$^5$ .................... C07C 247/04; C07C 43/11; C07C 43/115; C06B 45/10
[52] U.S. Cl. .................................... 552/10; 149/196; 552/11
[58] Field of Search .................... 149/19.6; 552/10, 11

[56] References Cited

U.S. PATENT DOCUMENTS

| | | | |
|---|---|---|---|
| 2,327,053 | 8/1943 | Marple et al. | 260/611 |
| 2,380,185 | 7/1945 | Marple | 260/615 |
| 3,305,565 | 2/1967 | Mueller | 260/348 |
| 3,310,504 | 3/1967 | Vandenberg | 260/2 |
| 3,331,788 | 7/1967 | Lorensen | 260/2 |
| 3,415,902 | 10/1968 | Hickner | 260/549 |
| 3,450,774 | 6/1969 | Vandenberg | 260/615 |
| 3,558,722 | 1/1971 | Kobayashi | 260/615 |
| 3,636,163 | 1/1972 | Jenkner | 260/615 |
| 3,642,705 | 2/1972 | Zollinger | 260/77.5 |
| 3,645,917 | 2/1972 | Vandenberg et al. | 260/2 |
| 3,875,189 | 4/1975 | Petty | 260/348 |
| 4,072,638 | 2/1978 | Boulet et al. | 260/2.5 |
| 4,173,710 | 11/1979 | Boulet et al. | 568/614 |
| 4,234,745 | 11/1980 | Phillips et al. | 568/614 |
| 4,268,450 | 5/1981 | Frankel | 260/349 |
| 4,288,262 | 8/1981 | Flanagan et al. | 149/19.6 |
| 4,303,414 | 12/1981 | Frankel et al. | 44/327 |
| 4,340,749 | 7/1982 | Patel | 560/182 |
| 4,379,894 | 4/1983 | Frankel et al. | 525/403 |
| 4,379,903 | 4/1983 | Reed, Jr. et al. | 528/55 |
| 4,391,970 | 7/1983 | Okamoto | 528/408 |
| 4,391,994 | 7/1983 | Kogoma et al. | 568/593 |
| 4,393,199 | 7/1983 | Manser | 528/408 |
| 4,405,497 | 9/1983 | Young et al. | 252/431 R |
| 4,431,845 | 2/1984 | Young et al. | 568/606 |
| 4,451,618 | 5/1984 | Okamoto | 525/349 |
| 4,486,351 | 12/1984 | Earl | 260/349 |
| 4,490,560 | 12/1984 | Yu et al. | 568/614 |
| 4,511,742 | 4/1985 | Yu | 568/614 |
| 4,653,690 | 3/1987 | St. Armand | 149/87 |
| 4,707,199 | 11/1987 | Sayles | 149/19.6 |
| 4,879,419 | 11/1989 | Johannesen | 568/606 |
| 4,962,213 | 10/1990 | Frankel et al. | 552/12 |

FOREIGN PATENT DOCUMENTS

| | | |
|---|---|---|
| 42965 | 9/1958 | Australia . |
| 49292 | 1/1959 | Australia . |
| 2343 | 1/1961 | Australia . |
| 6871 | 4/1961 | Australia . |
| 16860 | 1/1963 | Australia . |
| 36910 | 10/1963 | Australia . |
| 52984 | 1/1964 | Australia . |
| 55373 | 2/1965 | Australia . |
| 1347 | 1/1966 | Australia . |
| 4590 | 8/1966 | Australia . |
| 64461 | 8/1969 | Australia . |
| 47100 | 1/1979 | Australia . |
| 52193 | 10/1979 | Australia . |
| 0042505 | 3/1988 | European Pat. Off. . |
| 872106 | 7/1961 | United Kingdom . |
| 1155713 | 4/1970 | United Kingdom . |
| 1229235 | 4/1971 | United Kingdom . |
| 1551902 | 9/1979 | United Kingdom . |
| 2021606 | 3/1983 | United Kingdom . |

OTHER PUBLICATIONS

W. Huber, "Titration in Nonaqueous Solvents", Academic Press, New York, N.Y., 1967, p. 215.
"Rocket Propulsion Elements", G. P. Sutton et al., John Wiley and Sons, New York, 4th Ed. Chap. 11 (1967).
E. J. Geothols, Adv. Polym. Sci., 23, 104 (1977).
H. M. Flowers, "Protection of the Hydroxyl Group", The Chemistry of the Hydroxyl Group, Part 2, S. Patai, Ed., Interscience Publishers New York, (1971), pp. 1001-1044.
C. B. Reese, Ed., "Protection of Alcoholic Hydroxyl Groups and Glycol Systems", Ch. 3, Protection of Alcoholic Hydroxyl Groups in Organic Chemistry, J. F. McOmie, Ed., Plenum Press, New York (1973).

Primary Examiner—Edward A. Miller
Attorney, Agent, or Firm—Gary L. Griswold; Walter N. Kirn; Eloise J. Maki

[57] ABSTRACT

Epichlorohydrin is polymerized with an active hydrogen-containing initiator and the resulting secondary hydroxyl-containing polyepichlorohydrin is further reacted to produce a hydroxyl-terminated polyepichlorohydrin product having chains terminating in a primary hydroxyl group, said polyepichlorohydrin product being reactable with an inorganic azide to produce a poly(glycidyl azide) product useful as a binder for solid rocket propellants.

9 Claims, No Drawings

PRIMARY HYDROXYL-TERMINATED POLYGLYCIDYL AZIDE

This is a continuation of application Ser. No. 361,945, filed Jun. 5, 1989, now abandoned, which is a division of application Ser. No. 771,253, filed Aug. 30, 1985, now abandoned.

This invention relates to hydroxyl-terminated polymers of epichlorohydrin and their preparation. In another aspect, it relates to azide derivatives of said polymers. In another aspect, it relates to polyurethanes of said epichlorohydrin polymers and their azide derivatives. In a still further aspect, it relates to solid rocket propellants using as a binder a polyurethane prepared from glycidyl azide polymers derived from polyepichlorohydrin.

The acid-catalyzed (or cationic) ring-opening or polymerization of epichlorohydrin in the presence of active hydrogen-containing initiators, mainly hydroxyl-containing molecules, e.g., water or alcohols (including polyols), to yield hydroxyl-terminated epichlorohydrin derivatives, is known. U.S. Pat. Nos. 4,340,749 (Patel), 4,391,970 (Okamoto), and 4,431,845 (Young et al) describe some recent improvements.

Known polyepichlorohydrin polyols generally have predominately (i.e., greater than about 90 percent) chain terminal groups containing secondary hydroxyl groups, —OCH$_2$CH(CH$_2$Cl)OH, with little if any chain terminal units containing primary hydroxyl groups, —CH$_2$OH. The secondary hydroxyl groups react relatively slowly with desired reactants, for example isocyanates, when compared to primary hydroxyl groups, and permit undesired side reactions, for example the reaction of isocyanates with water or carbamate moieties.

Somewhat incidentally, European Patent Application 0 042 505 A3 A discloses polyether polyols having one terminal unit containing a secondary hydroxyl group and another terminal unit containing two hydroxyl groups separated by 2, 3, or 4, carbon atoms, one or both of which may be primary. Although these primary hydroxyl groups would also react fast, for example with isocyanates, the resultant products would have regions of high crosslink density (and, thus, relatively poor elastomeric properties) because of the close proximity of these hydroxyl groups.

An important polymeric derivative of polyepichlorohydrin polyols, prepared by displacement of chloride by azide (see, for example, U.S. Pat. Nos. 4,268,450, 4,379,894, and 4,486,351), is hydroxyl-terminated glycidyl azide polymer useful in energetic compositions such as rocket propellants, gun propellants, and gas generating compositions. The azide polymer has chains of repeating units, [CH$_2$CH(CH$_2$N$_3$)O]$_n$, each chain terminating with a secondary hydroxyl-containing unit, —CH$_2$CH(CH$_2$N$_3$)OH. The hydroxyl groups of the polyepichlorohydrin precursor remain intact as they are unaffected by the displacement reaction and allow the azide polymer made in this way to react with polyisocyanates, albeit slowly with consequent undesired side reactions.

It is an object of this invention to provide hydroxy-terminated polyepichlorohydrin polyols with enhanced isocyanate-reactive hydroxyl-group termination.

It is another object of this invention to prepare glycidyl azide polymer with hydroxyl group termination of enhanced isocyanate-reactivity so that undesired side reactions are minimized and the polymer is better-suited for use in castable, curable, energetic compositions.

It is another object of this invention to provide hydroxy-terminated polyepichlorohydrin with the maximum practicable amount of displaceable chloride so that the highest energy glycidyl azide polymer may be produced therefrom.

It is another object of this invention to provide polyepichlorohydrin polyol with only a single terminal hydroxy group on each chain end in order that highly desirable elastomeric mechanical properties may be obtained.

It is another object of this invention to provide polyepichlorohydrin polyols and their hydroxyl-functional derivatives with a sufficiently high fraction of more reactive hydroxyl functionality to significantly decrease the curing time of the polyol with polyisocyanates, relative to the curing time of currently available polyepichlorohydrin polyols.

It is yet another object of this invention to provide a glycidyl azide polymer which can be suitably cured with polyisocyanate.

This invention provides, in one aspect, hydroxyl-terminated polyepichlorohydrin product with a hydroxyl functionality of up to 4 or more, comprising polymer, which is preferably a polyol, e.g. a diol, having polyepichlorohydrin homopolymer chains, [CH$_2$CH(CH$_2$Cl)O]$_n$, each bonded at its terminus to a moiety which is the site of said functionality, which chains make up the major portion (i.e., greater than 50 percent and preferably greater than 80 percent) of the product by weight, a significant amount of said chains terminating in a moiety containing a single hydroxyl group which is a primary hydroxy group, preferably a moiety of the structure (RCH$_2$O),H where R is a divalent organic group, for example an aliphatic group with 1 to 10 carbon atoms, e.g. —CH$_2$— or —CH(CH$_2$Cl)—, and z is a number of 1 to 6. Generally, the amount of such chains terminated with said primary hydroxy-containing moiety will be at least about 20 percent, and generally 20 to 50 percent or preferably up to 90 percent or higher, with the balance, if any, of the chains making up the product terminating predominantly in a moiety containing a single hydroxyl group which is a secondary hydroxyl group, such moiety preferably having the structure —CH$_2$CH(CH$_2$Cl)OH.

The polyepichlorohydrin product of this invention is generally normally liquid and has a number average molecular weight, for example, of 500 to 10,000 and, preferably a relatively narrow molecular weight distribution or low polydispersity which is generally less than 1.5, preferably less than 1.2, e.g., less than about 1.5 for a 2000 molecular weight product and more preferably less than about 1.2 for such product. The polyepichlorohydrin product preferably contains only a relatively minor amount, e.g., less than 2 weight percent per 1000 molecular weight of product, of low molecular weight, non-hydroxyl functional, cyclic ether oligomers which generally have 2 or 4 epichlorohydrin units cyclized, or more preferably essentially none of such oligomer. Such low polydispersity and low oligomer content of the product are advantageous because, for example, the derivatives thereof such as the polyurethanes of such product and the glycidyl azide derivative have better mechanical propeties, such as higher tensile strength.

The hydroxyl-terminated polyepichlorohydrin products, and the derivatives thereof (such as the glycidyl azide polymer derivatives) with the hydroxyl groups of the precursor polyepichlorohydrin intact, have enhanced reactivity with isocyanates and other reactants as compared to polyepichlorohydrin polyols (and azide derivatives) having essentially only secondary hydroxyl groups. Such enhanced reactivity results in elastomeric polyurethane products which will have better mechanical properties, such as elongation, tensile strength, density, and modulus, an important factor where such products are used, for example, as binder for energetic compositions such as those described in the patents mentioned above.

A class of the hydroxyl-terminated polyepichlorohydrin products of this invention, described above, comprise generally a polymer or mixture of polymers which can be represented by the general formula:

$$Q[(E)_n(RCH_2O)_aH]_m \qquad I$$

where
Q is an organic radical, such as $H(OCH_2R)_aO)-$, $-OC_2H_4O-$, or $-OCH_2C_6H_{10}CH_2O-$, or a heteroatom such as $-O-$, or a heteroatom moiety, such as $-OH$;
E is an epichlorohydrin (or chloromethylethyleneoxy) unit;
n is a number greater than 1, e.g. 2 to 50;
$(E)_n$ is a polyepichlorohydrin chain;
R is a divalent organic linking group, for example an aliphatic group with 1 to 10 carbon atoms, such as $-(CH_2)_m$, $-CH(CH_2Cl)-$, or $-C(O)CH_2CH_2-$;
a is a number of 0 to 6 with the proviso that the average value of subscript greater than zero, preferably 1 to 2, and such that a significant amount, e.g., at least about 20 percent, of the hydroxyl groups in the products are primary; and
m is a number of 1 to 6.

Subclasses of the hydroxyl-terminated polyepichlorohydrin products described above are those comprising polymer represented by one of the general formulas:

$$G[(E)_n(R^1CH_2O)_aH]_m \qquad II-1$$

$$G[(E)_nR^2CH_2OH]_m \qquad II-2$$

$$HOCH_2R^3O(E)_nH \qquad III$$

$$HOCH_2R^3O(E)_n(R^1CH_2O)_aH \qquad IV-1$$

$$HOCH_2R^3O(E)_nR^2CH_2OH \qquad IV-2$$

$$[HOCH_2R^3O(E)_n]_pZ^1 \qquad V-1$$

$$[HOCH_2R^3O(E)_n]_pZ^2 \qquad V-2$$

where, in the above formulas,
E, $(E)_n$, n, a, and m are as defined for formula I;
G is an oxygen atom or the residue of an organic polyhydroxyl compound (such as the active hydrogen-free residue of an initiator for the polymerization of epichlorohydrin), e.g., $-OCH_2CH_2O-$, $-O(CH_2)_3O-$, $-O(CH_2)_4O-$, $-OCH_2C_6H_{10}CH_2O-$, $-OCH_2CH(CH_2Cl)O-$, $CH_3CH_2C(CH_2O)_3$, $-OCH_2CH(CH_3)O-$, $C(CH_2O-)_4$, $-OC_6H_{10}O-$;
$R^1$ is a divalent organic group, for example an aliphatic group with 1 to 10 carbon atoms, (such as derived from a cyclic chain extender, e.g. ethylene oxide, reacted with a hydroxyl group of a polyepichlorohydrin), e.g., $-CH_2)_b$, $-CO(CH_2)_b$, $-CH_2C(CH_3)_2-$, $-CH_2(CH_2Cl)_2-$, and $-CH_2CH_2OCH_2-$, where b is a number of 1 to 6,
$R^2$ is a divalent organic group, for example an aliphatic group with 1 to 10 carbon atoms, (such as that derived from a blocked chain extending reagent), e.g., $-(CH_2)_b$, $-CO(CH_2)_b-$, $-CH(CH_2Cl)-$, $-CH_2C(CH_3)_2-$, $-CH_2CH(CH_3)-$, $-CONH(CH_2)_b$, and $-CH_2C_6H_{10}-$, and b is as defined above;
$R^3$ is a divalent organic group, for example an aliphatic groups with 1 to 10 carbon atoms, (such as derived from a blocked initiator) which is stable under epichlorohydrin polymerization conditions, e.g., $-(CH_2)_b$, $-CH(CH_2Cl)-$, $-C(CH_2)_2-$, $-CO-$, $-(CH_2)_2CO-$, $-C(CH_2Cl)_2CH_2-$, $-C(CH_3)_2CH_2-$, $-CH(CH_3)-$, $-CH_2OCH_2(CH_2)_b$, and b is as defined above;
p is a number equal to the valence of $Z^1$ or $Z^2$, which valence is 1 to 6;
$Z^1$ is a linking group which is the residue of a hydroxyl-reactive reagent; for example, where p is 2, $Z^1$ can be, for example,

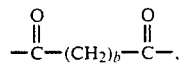

$-CH_2C_6H_{10}CH_2-$, $-CH_2C\equiv CCH_2-$,

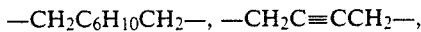

 $-CO-$, $-CH_2CH_2OCH_2CH_2-$, $-Si(R)_2-$, or $-RPO-$ where R represents a non-functional monovalent organic group, such as lower alkyl, e.g. methyl or aryl, e.g. phenyl, or, where p is 3, $Z^1$ can be, for example, $C_6H_3(CO-)_3$, $CH_3CH_2C(CH_2-)_3$,

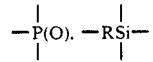

or $C_6H_3(CH_2-)_3$, where R is as defined above, or, where p is 4, $Z^1$ can be, for example, $C(CH_2-)_4$, $C_6H_2(CO-)_4$, or

and
$Z^2$ is the group formed from a linking reagent which reacts with hydroxyl groups by an addition process, e.g, where p is 1, $Z^2$ can be, for example, $-CONHCH_2CH_2OCOC(CH_2)=CH_2$, or, where p is 2, $Z^2$ can be, for example, $-CONH(CH_2)_bNHCO$, $CH_3C_6H_3(NHCO-)_2$, or $C_6H_4(NHCO-)_2$, and, where p is 3, $Z^2$ can be, for example, $C_6H_3(NHCO-)_3$.

The following is a description of illustrative reaction schemes for the preparation of the above-described hydroxyl-terminated polyepichlorohydrin products of this invention. These schemes generally involve known conventional techniques, such as the use of hydroxyl-blocking reagents which is described, for example, by H. M. Flowers, "Protection of the Hydroxyl Group", p. 1001–1044, in "The Chemistry of the Hydroxyl Group", Part 2, S. Patai, Ed., Interscience Publishers, New York (1971), and C. B. Reese, Ed., "Protection of Alcoholic Hydroxyl Groups and Glycol Systems," p. 95–120, in "Protective Groups in Organic Chemistry", J. F. McOmie, Ed., Plenum Press, New York (1973).

As illustrated by the following schemes, the hydroxyl-terminated polyepichlorohydrin products of this invention can be made by polymerizing epichlorohydrin with an active-hydrogen-containing initiator, e.g. an alcohol, which is conventional (Schemes II-1, -2) or preferably contains one blocked, primary hydroxyl group (Schemes III, IV-1, 2, V-1, 2). The resulting secondary hydroxyl-containing polyepichlorohydrin intermediate is preferably reacted with a cyclic or blocked, primary hydroxyl-producing, hydroxyl-reactive, chain-extending reagent (Schemes IV-1 or -2), or with a connecting reagent that reacts by a condensation mechanism (Scheme V-1) or addition mechanism (Scheme V-2) to connect the polyepichlorohydrin chains via their said secondary hydroxyl groups, and chemically or thermally removing the hydroxyl-blocking groups, where present, from the resulting extended or connected polyepichlorohydrin. Alternatively (Scheme III), the polyepichlorohydrin intermediate made using said blocked initiator is chemically or thermally unblocked to yield the product of the invention.

For the products of above general formula II-1 a secondary hydroxyl-terminated polyepichlorohydrin, A, such as described in the above-described patents, e.g., U.S. Pat. No. 4,431,845, is reacted with a cyclic, primary hydroxyl-producing, hydroxyl-reactive, chain-extending reagent, B, e.g. ethylene oxide or butyrolactone, in the presence of cationic ring-opening catalyst, e.g., $BF_3$, which reaction is illustrated by the following scheme.

SCHEME II-1

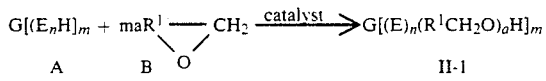

$$G[(E_nH]_m + maR^1\!-\!CH_2 \xrightarrow{catalyst} G[(E)_n(R^1CH_2O)_aH]_m$$

A    B    O                    II-1

For the products of above general formula II-2, a polyepichlorohydrin, A, like that described for Scheme II-1 is reacted with a blocked, primary hydroxyl-producing, hydroxyl-reactive, chain extending reagent, C, in the presence of an acid acceptor, such as sodium carbonate, 2,6-dimethylpyridine, or magnesium oxide. Representative chain extending reagents for this purpose are

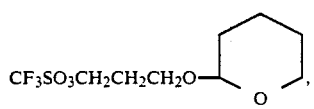

$CF_3SO_3CH_2CH_2CH_2O\!-\!\bigcirc_O$, $ClCOCH_2CH_2CH_2OCO_2C(CH_3)_3$, $OCN\!-\!CH_2CH_2OCO_2C(CH_3)_3$, and

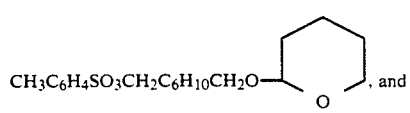

$CH_3C_6H_4SO_3CH_2C_6H_{10}CH_2O\!-\!\bigcirc_O$, and

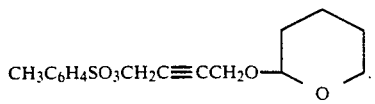

$CH_3C_6H_4SO_3CH_2C\!\equiv\!CCH_2O\!-\!\bigcirc_O$.

The resulting product, a blocked, primary hydroxyl-terminated polyepichlorohydrin, D, is then treated, for example thermally or chemically, e.g. with a dilute acid, to unblock intermediate D to yield the product of formula II-2. The above-described reaction and treatment are illustrated by the following scheme.

SCHEME II-2

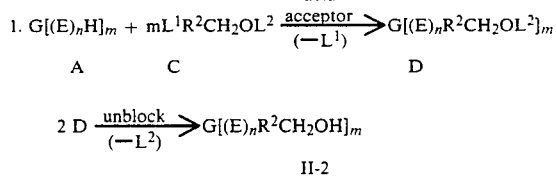

1. $G[(E)_nH]_m + mL^1R^2CH_2OL^2 \xrightarrow[(-L^1)]{acid\ acceptor} G[(E)_nR^2CH_2OL^2]_m$

A              C                                          D

2. $D \xrightarrow[(-L^2)]{unblock} G[(E)_nR^2CH_2OH]_m$

II-2

C represents the blocked, primary hydroxyl-producing, hydroxyl-reactive, chain-extending reagent having a divalent organic linking group $R^2$, a first leaving group $L^1$, and second leaving group $L^2$ such that $L^1$ can be displaced or undergo addition under conditions which do not affect $L^2$, the polymer backbone, or the pendant groups. $L^2$ can be removed under conditions which do not cleave the linkage between $(E)_n$ and $R^2$ or the ether linkage in the polyepichlorohydrin chain or adversely affect the pendant chloromethyl groups.

For the products of general formula III, the polymerization of epichlorohydrin is initiated with an active hydrogen-containing, preferably hydroxyl-functional, blocked-hydroxyl initiator, F, and the terminal primary hydroxyl group in the resulting polymer, J, is unblocked by chemically or thermally removing the blocking group. A scheme for the preparation of products of formula III is as follows:

SCHEME III

1. $L^3OCH_2R^3OH + nCH_2CHCH_2Cl \xrightarrow{catalyst}$

F

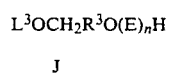

$L^3OCH_2R^3O(E)_nH$

J

2. $J \xrightarrow[(-L^3)]{unblock} HOCH_2R^3O(E)_nH$

III $L^3$ in the above scheme is a leaving group which is stable to the polymerization conditions but removable under conditions which do not disrupt the linkage between $R^3O$ and $(E)_n$ or the ether linkages in the polyepichlorohydrin chain and do not adversely affect the pendant chloromethyl groups. Representative blocked initiators, F, which can be used in Scheme III are $CF_3CO_2CH_2CH_2OH$ $CCl_3CO_2CH_2CH_2OH$ CF₃CO₂CH₂CH(CH₂Cl)OH CF₃CO₂CH₂C(CH₂Cl)₂CH₂OH CCl₃CO₂CH₂C(CH₃)₂CH₂OH

CH₃C₆H₄SO₃CH₂CH₂CH₂CH₂OH

C₃F₇CO₂CH₂CH₂CH₂OH (CH₃)₃COCO₂CH₂CH₂OH

H₂C=CHCO₂CH₂CH₂OH

CH₃C₆H₄SO₃CH₂C≡CCH₂OH

For the products of formula IV-1, the hydroxyl-blocked, polyepichlorohydrin intermediate J of Scheme III, having secondary hydroxyl terminal groups, —CH₂CH(CH₂Cl)OH, is chain extended by reacting it with a cyclic, primary hydroxyl-producing, hydroxyl-reactive, chain extending reagent B (described above in connection with Scheme II-1) in the presence of an acid catalyst, e.g., BF₃. The resulting extended polymer, M, is unblocked by a treatment like that d(R)scribed for Scheme III to yield the primary hydroxyl-terminated polyepichlorohydrin product IV-1. These reaction are illustrated in the following scheme.

SCHEME IV-1

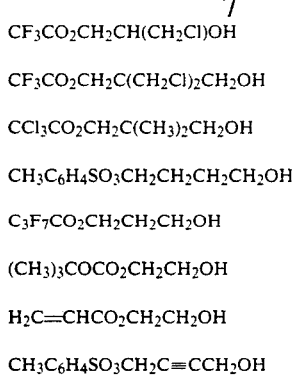

L³OCH₂R³O(E)ₙ(R¹CH₂O)ₐH

M

2. M $\xrightarrow[(-L^3)]{unblock}$ HOCH₂R³O(E)ₙ(R¹CH₂O)ₐH

IV-1

For the products of formula IV-2, the hydroxyl-blocked, polyepichlorohydrin intermediate J of Scheme III is reacted with a hydroxyl-blocked, primary hydroxyl producing hydroxyl-reactive, chain-extending reagent, C (described above in connection with Scheme II-2) to produce an intermediate polyepichlorohydrin product, N, the terminal hydroxyl groups of which are blocked. The intermediate product, N, is treated as described above in IV-2. A scheme for these reactions is as follows.

SCHEME IV-2

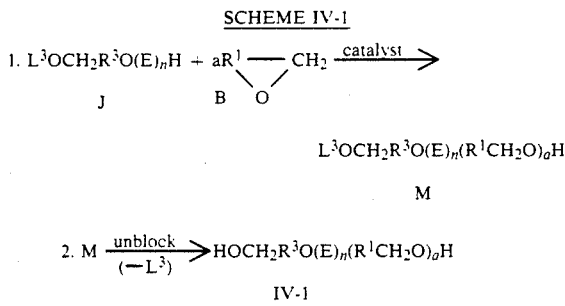

-continued
SCHEME IV-2

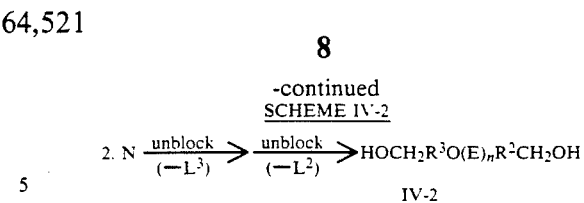

For the products of formula V-1, the hydroxyl-blocked, polyepichlorohydrin intermediate J of Scheme III is reacted with a connecting reagent, P, which reacts by a condensation mechanism, to form a hydroxyl-blocked polyepichlorohydrin intermediate, S, which is then unblocked by a treatment such as described in connection with Scheme II-2. A scheme for these reactions is as follows.

SCHEME V-1

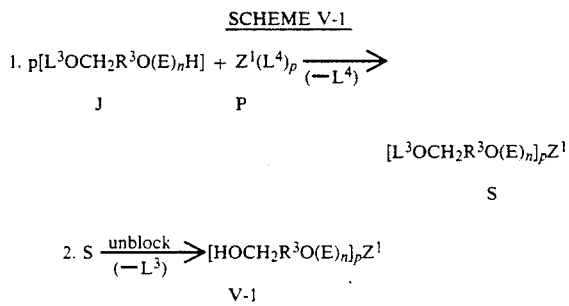

In the connecting reagent P, Z¹ is a group or atom of valence p and L⁴ is a leaving group displaceable by the secondary hydroxyl groups of the intermediate polymer J. Representative connecting reagents, P, which can be used in the above scheme, are phthalic anhydride, C₈F₁₇SO₂N(C₂H₅)CH₂COCl, ClCOCH₂CH₂COCl, C₆H₄(COCl)₂, (CF₃SO₃)₂C₄H₈, (CH₃C₆H₄SO₃)₂C₂H₄, (CH₃)₂SiCl₂, C₆H₅P(O)Cl₂, COCl₂, CH₂O, ClCOC(CH₃)₂CH₂CH(CH₃)CH₂COCl, C₆H₃(COCl)₃, CH₃CH₂C(CH₂OSO₂CF₃)₃, POCl₃, CH₃SiCl₃, C₆H₂(COCl)₄, SiC₄, and CH₃C₆H₄SO₃CH₂C≡CC-H₂O₃C₆H₄CH₃.

For products of formula V-2, the hydroxyl-blocked, polyepichlorohydrin intermediate J of Scheme III is reacted with a connecting reagent, Z³, which reacts by an addition mechanism, to form a hydroxyl-blocked polyepichlorohydrin adduct, T, which is unblocked by a treatment such as described in connection with Scheme II-2. A scheme for the preparation of products V-2 is as follows:

SCHEME V-2

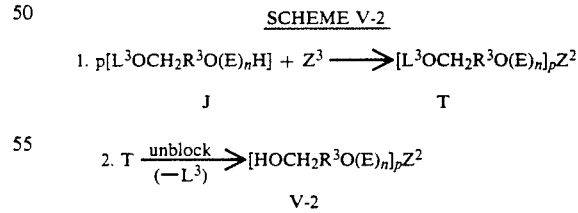

In the above scheme, Z² is a linking group derived from Z³, by addition of active hydrogen(s). Representative examples of Z³ and Z² are:

| Z³ | Z² |
| --- | --- |
| C₇F₁₅CH₂NCO | C₇F₁₅CH₂NHCO— |
| CH₂=C(CH₃)CO₂CH₂CH₂NCO, | CH₂=C(CH₃)CO₂CH₂CH₂NHCO— |
| OCN(CH₂)₆NCO | —CONH(CH₂)₆NHCO— |

| $Z^3$ | $Z^2$ |
|---|---|
| $OCN(C_6H_4)NCO$ | $-CONHC_6H_4NHCO-$ |

If $Z^1$ or $Z^2$ is monofunctional, joining in Schemes V-1 and V-2 will not take place but a selected group may be attached to the blocked polymer. In this way a polyepichlorohydrin polymer may be prepared with a primary hydroxyl group on one end and a group which would have interfered with polymerization on the other end, e.g. a carboxylic acid or a chelating agent or a tertiary amine. It is within the scope of this invention to use a joining reagent, $Z^1$ or $Z^2$ in Schemes V-1 and V-2, which has displaceable groups which may be converted to azide or to some other group in a subsequent modification of the products V-1 and V-2.

In the preparation of the products of general formulas II-1 and II-2 in accordance with corresponding Schemes II-1 and II-2, the secondary hydroxyl-terminated polyepichlorohydrin intermediate A can be prepared by polymerization of epichlorohydrin using hydroxyl-functional initiators and known epichlorohydrin polymerization catalysts, such as triethyloxonium hexafluorophosphate, boron trifluoride etherate, or the combination of a fluorinated acid and a polyvalent organotin compound, e.g., diphenyldibutyltin, as described in U.S. Pat. No. 4,431,845. However, the catalyst preferred is anhydrous stannic chloride per se or in combination with a strong carboxylic acid (i.e., one having a $pK_a$ of less than about 2, preferably less than about 1) and a co-catalyst, such as trifluoroacetic acid or trichloroacetic acid. A scheme illustrating the preferred preparation of the polyepichlorohydrin intermediate A is as follows.

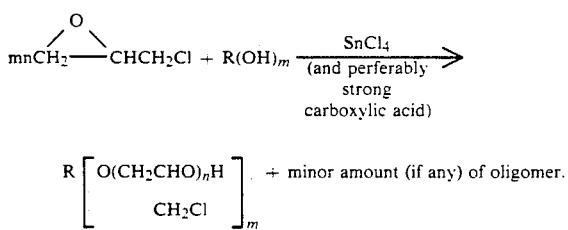

In the above equation, R is an organic radical, e.g, containing 1 to 20 carbon atoms, such as an aliphatic radical or aromatic radical or combination of such radicals, which can contain or be substituted with moieties that are unreactive with epichlorohydrin or the desired product and do not adversely affect the polymerization or the desired product, such as halo, oxy, carbonyl, or combinations of such moieties, e.g, ester. For example, R can be $CH_3-$, $ClCH_2CH_2-$, $CH_3CH_2CH_2CH_2-$, $C_6H_5CH_2-$, $-CH_2C_6H_{10}CH_2-$, $-(CH_2)_x-$, where x is 3 to 8, $-CH(R'')CH(R')-$ and $-CH(R')CH_2CH(R')-$ where R, is selected from H and a lower alkyl, such as $CH_3-$, $CH_2Cl-$, and $C_2H_5-$, and R'' is said lower alkyl,

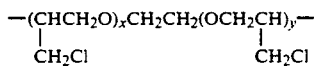

where $x+y$ is 1 to 20, $-CH_2C_6H_4CH_2-$, and $CH_3C(CH_2-)_3$. The subscript m is 1, 2, 3 or 4, and n is at least 2 and, where R has a molecular weight of less than 1000, n is a number such that the polyepichlorohydrin i.e., poly(chloromethylethyleneoxy), portion of the product is the major portion of the product by weight, n generally being 2 to about 100.

Poly(glycidyl azide) polymer derivatives, described hereinafter, of the polyepichlorohydrin polymers can be represented by formulas like I to V-2 except that Cl is replaced by $N_3$. Such derivatives will generally have approximately the same low polydispersity and low oligomer content as their polyepichlorohydrin precursors when prepared by the anhydrous $SnCl_4-$ catalyzed process.

The strong carboxylic acid used as a co-catalyst in preparing polyepichlorohydrin precursors A generally increases the epichlorohydrin polymerization reaction rate as compared to the reaction rate obtained when it is not used, i.e., when just the stannic chloride catalyst is used; for example, the time for complete conversion of the epichlorohydrin at 65°–70° C. is reduced from about 24 hours to about 1 hour when the co-catalyst is used with the stannic chloride. The use of co-catalyst with the $SnCl_4$ also allows a lower amount of stannic chloride catalyst to be used, e.g., about $\frac{1}{3}$ the amount. And the use of the co-catalyst, which speeds up the reaction rate, still generally results in a hydroxyl-terminated polyepichlorohydrin reaction product of light color, e.g., a Gardner color of less than 2, and low polydispersity and with lower amounts, if any, of the cyclic ether oligomers as compared to when the stannic chloride is used as the only catalyst.

The initiators used in the polymerization of epichlorohydrin are unreactive with the polymerization catalyst, e.g. stannic chloride, the preferred catalyst. Representative illustrative initiators which can be used include monohydric aliphatic alcohols, such as $CH_3OH$, $C_2H_5OH$, $(CH_3)_2CHOH$, $CH_3(CH_2)_3OH$, $ClC_2H_4OH$, and $CH_3(CH_2)_{16}CH_2OH$, monohydric cycloaliphatic alcohols, such as $C_6H_{11}CH_2OH$, polyhydric aliphatic alcohols, such as $CH_2(CH_2OH)_2$, $HOCH_2CH(CH_3)OH$, $C_2H_4(CH_2OH)_2$, $HOCH_2CH(CH_2Cl)OH$, and $CH_3CH(OH)C_2H_4OH$, aromatic alcohols, such as $C_6H_5CH_2OH$, and polyhydric cycloaliphatic alcohols, such as

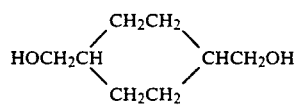

and the hydroxyl-containing organic compounds disclosed in said U.S. Pat. No. 2,327,053 which are unreactive with stannic chloride. Initiators which are polymeric in nature can also be used, such as a low molecular weight hydroxyl-functional polyepichlorohydrin, hydroxyl-functional poly(ethyleneterephthalate), hydroxyl-functional perfluoropoly(oxyalkylene), such as $HOCH_2CF_2O(CF_2O)_x(CF_2CF_2O)_yCF_2CH_2OH$, hydroxyl-functional poly(oxyethylene), and hydroxyl-functional poly(oxypropylene). Other hydroxyl-containing organic monomeric or polymeric materials which can be used are those disclosed in said U.S. Pat. No. 4,431,845 which are unreactive with stannic chloride. Fluoroaliphatic alcohols which can be used are those such as $C_8F_{17}SO_2N(C_2H_5)CH_2CH_2OH$ and $C_8F_{17}SO_2N(CH_2CH_2OH)_2$, and those disclosed in said U.S. Pat. No. 4,340,749 which are unreactive with stannic chloride. Mixtures of such initiators also can be used.

The applicability of an alcohol or hydroxyl-containing organic material as an initiator for epichlorohydrin polymerization can be simply determined by mixing 1 part of the anhydrous stannic chloride with 5 to 10 parts of the hydroxyl material in about 30 parts of 1,2-dichloroethane solvent, heating the resulting mixture, e.g., 70° C. for 1 hour, and observing whether an irreversible reaction occurs, for example, by evidence of a precipitate or evolution of hydrogen chloride. If no such reaction occurs, the hydroxyl material can be used as an initiator. Materials which have been found to be so reactive, and thus not suitable as an initiator, include ethylene glycol.

Where the stannic chloride is used without the co-catalyst, 1,4-butane diol is not a preferred initiator since the use of the diol results in appreciable amounts of oligomer.

By controlling the proportions of epichlorohydrin to initiator, it is possible to limit the degree of polymerization and, consequently, the molecular weight of the polyepichlorohydrin product. Thus, the molar ratio of epichlorohydrin to hydroxyl group in the initiator may be in the range of about 2:1 to 100:1.

The stannic chloride catalyst employed in the process is a hydrolyzable compound in the presence of water. Furthermore, its catalytic activity is considerably impaired when it is in a hydrolyzed condition and larger amounts of such catalyst are required to effect the polymerization reaction when the reactants contain appreciable amounts of water as compared to when they are substantially dry. Also, the hydrogen chloride liberated by the hydrolysis of the stannic chloride may combine with the epichlorohydrin to form chlorohydrin by-products which may undesirably act as initiators. It is therefore preferable that the reactants used in the epichlorohydrin polymerization be in substantially anhydrous condition.

The amount of stannic chloride catalyst to be used without the co-catalyst in preparing the preferred polyepichlorohydrin intermediate A is that amount sufficient to result in generally substantially quantitative or preferably essentially complete conversion of the epichlorohydrin to the polyepichlorohydrin product, and the amount of stannic chloride to be used will depend on the desired molecular weight of such product. Generally, for a product having a desired molecular weight of about 2000, such amount of stannic chloride will be about 0.5 to 1 weight percent of the polymerization reaction mixture; for a product with a molecular weight of 4000, such amount of stannic chloride will be about 1 to 2 weight percent; and for a product with a molecular weight of 1000, such amount will be about 0.25 to 0.5 weight percent.

As discussed above, the preferred epichlorohydrin polymerization process employs a strong carboxylic acid as a co-catalyst. When such co-catalysts are used, 1,4-butane diol can be used as an initiator without resulting in the formation of appreciable amounts of the cyclic oligomer. Generally, the strong carboxylic acid co-catalysts used are those having a $pK_a$ of less than 2 and preferably less than 1, as determined, for example, by the method described by W. Huber, "Titration in Nonaqueous Solvents," Academic Press, New York, NY, 1967, p. 215. A class of such acid co-catalysts can be represented by the formula R—CXY—COOH, where X and Y are independently selected from the group consisting of chlorine and fluorine, and R is hydrogen, fluorine, chlorine, or a moiety which is electron-withdrawing (relative to hydrogen), e.g., —$C_2F_5$ and —$C_6H_5$, and does not adversely affect the polymerization. Representative co-catalysts (and their $pK_a$ values) include trifluoroacetic acid (0.23), trichloroacetic acid (0.66), and dichloroacetic acid (1.25).

The amount of co-catalyst used is that which, together with the stannic chloride catalyst, is sufficient to minimize the formation of the cyclic ether oligomeric by-products. Such amount generally will also, as compared to using the stannic chloride as the sole catalyst, increase the reaction rate and permit use of less stannic chloride. Generally, the molar ratio of stannic chloride to co-catalyst will be 1:0.5 to 1:10, preferably 1:3 to 1:5, higher amounts of the co-catalyst in these ranges acting significantly as an initiator and thus influencing the molecular weight of the polyepichlorohydrin product.

The epichlorohydrin polymerization can be carried out in the presence of a solvent or inert diluent, for example, where the alcohol initiator is a solid, suitable solvents for this purpose representatively including 1,2-dichloroethane, benzene, toluene, methylene chloride, and carbon tetrachloride. The catalyst(s) can be added to the reaction vessel containing the initiator and solvent and the epichlorohydrin can be then incrementally added. Prior to adding the epichlorohydrin, and during its addition and the ensuing reaction, the reaction vessel is heated or cooled to a desired polymerization temperature, e.g., about 0° C. to 110° C., preferably 65° to 75° C. The polymerization reaction is conducted under anhydrous conditions and to that end a slow, dry nitrogen gas purge of the reaction vessel can be used. The reaction pressure is generally the autogenous pressure but superatmospheric pressures can be used, e.g., up to 10 atmospheres, where the more volatile initiators are used.

Generally, completion of the reaction will be indicated by the cessation of the reaction exotherm and the leveling-off of the viscosity increase of the reaction mixture. Completion of the reaction can be verified by measuring the weights of reaction mixture samples before and after they are heated to remove volatile materials.

The resulting secondary hydroxyl-terminated polyepichlorohydrin product A can be recovered by subjecting the reaction product mixture to reduced pressure to remove solvent and volatile material, e.g., unreacted epichlorohydrin, adding further solvent, and then extracting the non-volatile material with an extracting agent, such as aqueous organic solvent, e.g., alcohol such as methanol, containing ammonium hydroxide, or preferably a chelating agent for tin such as the tetrasodium salt of ethylenedinitrilotetracetic acid, used in an amount of about 5 to 10 percent in excess of the equivalent amount necessary to complex with the stannic chloride and neutralize the acid co-catalyst (if present). The resulting two phases are separated, the heavier phase containing the desired polyepichlorohydrin product and the other phase being the aqueous organic solvent containing the chelating agent and catalysts. The product phase can be washed several additional times with aqueous organic solvent. The washed product can be stripped under reduced pressure.

The conversion of the epichlorohydrin to the secondary hydroxyl-terminated polyepichlorohydrin product by the preferred epichlorohydrin polymerization process is generally substantially quantitative and usually at least 95 percent based on the epichlorohydrin reactant, and typically 98 to 100 percent when the co-catalyst is used with the stannic chloride. The amount of the cyclic oligomer by-product is a minor amount of the polyepichlorohydrin product, generally less than 2 weight percent per 1000 molecular weight of product, and in the case where the co-catalyst is used with the stannic chloride, less than 0.5 weight percent per 1000 molecular weight of product.

In preparing the hydroxyl-blocked polyepichlorohydrin intermediate J used in the above Schemes III, IV-1, IV-2, V-1, and V-2, by polymerization of epichlorohydrin in the presence of a hydroxyl-blocked, hydroxyl-functional initiator F, said known epichlorohydrin polymerization catalysts can be used. However, the catalyst preferred is the above-described catalyst used in preparing the secondary hydroxyl-terminated polyepichlorohydrin A, namely anhydrous stannic chloride per se or in combination with said strong carboxylic acid.

The hydroxyl-terminated polyepichlorohydrin products of this invention can be converted to polyurethanes by reaction with polyisocyanate chain extension agents or crosslinking agents, or to polyesters by reaction with polycarboxylic acids. For example, the products can be reacted with polyisocyanates, e.g., diphenylmethane diisocyanate, hexamethylene diisocyanate, isophorone diisocyanate, a biuret trimer of hexamethylene diisocyanate ("Desmodur" N-100), p-phenylene diisocyanate, 2,4- and/or 2,6-tolylene diisocyanates, in a conventional urethane reaction to form elastomeric polyurethanes used, for example, as foams for upholstery, automobile bumpers, and high performance coatings. The polyepichlorohydrin products can also be reacted with tertiary amines to form water-soluble polymeric quaternary salts used as plating bath additives.

The hydroxyl-terminated polyepichlorohydrin products of this invention may be converted in a conventional manner with inorganic azides, such as sodium azide, to normally liquid hydroxyl-terminated glycidyl azide polymers, the reaction resulting in displacement of chlorine from the —$CH_2Cl$ pendant groups by azide ion, $N_3$ to form —$CH_2N_3$ pendant groups.

Detailed descriptions of suitable procedures which can be used in this invention for displacing chlorine by azide are set forth in the prior art (e.g. U.S. Pat. Nos. 4,268,450 (Frankel et al), 4,288,262 (Flanagan), 4,379,894 (Frankel et al), and 4,486,351 (Earl)).

This invention provides, in another aspect, hydroxyl-terminated poly(glycidyl azide) product with a hydroxyl functionality of up to 4 or more, comprising a polymer, which is preferably a polyol, e.g. diol, having poly(glycidyl azide) homopolymer chains, [$CH_2CH(CH_2N_3)O]_n$, which make up the major portion (i.e., greater than 50 percent and preferably greater than 80 percent) of the product by weight, a significant amount of said chains terminating in a moiety containing a single hydroxyl group which is a primary hydroxy group, preferably a moiety of the structure —(R'C$H_2O)_zH$ where R' is a divalent organic group, for example, —$CH_2$— or —$CH(CH_2N_3)$—, and z is a number from 1 to 6. Generally, the amount of such chains terminated with said primary hydroxy-containing moiety will be at least about 20 percent, and generally 20 to 50 percent or preferably up to 90 percent or higher, the balance, if any, of the chains terminating predominantly in a moiety containing a single hydroxyl group which is a secondary hydroxyl group, such moiety preferably having the structure —$CH_2CH(CH_2N_3)OH$. The product is generally normally liquid and has a number average molecular weight, for example, of about 500 to 10,000 and preferably a relatively narrow molecular weight distribution or low polydispersity which is generally less than 1.5, preferably less than 1.2, e.g., less than about 1.5 for a 2000 molecular weight product and more preferably less than about 1.2 for such product. The preferred poly(glycidyl azide) product preferably contains only a relatively minor amount, e.g., less than 2 weight percent, per 1000 molecular weight of product, of low molecular weight, non-hydroxyl functional, cyclic ether oligomers which generally have 2 or 4 azidomethylethyleneoxy units cyclized, or preferably essentially none of such oligomer.

A class of the hydroxyl-terminated poly(glycidyl azide) products of this invention, described above, comprise generally a polymer or mixture of polymers which can be represented by the general formula:

$$Q'[(E')_n(R'CH_2O)_aH]_m \qquad \text{VI}$$

where

Q' is an organic radical, such as H(OCH$_2$R')$_a$O—, —$OC_2H_4O$—, or —$OCH_2C_6H_{10}CH_2O$—, or a heteroatom such as —O—, or a heteroatom moiety, such as —OH;

E' is an azidomethylethyleneoxy unit;

n is a number greater than 1, e.g. 2 to 50;

(E')$_n$ is a poly(glycidyl azide) chain;

R' is a divalent organic linking group, such as +CH$_2$+$_m$, —CH(CH$_2$N$_3$)—, or —C(O)CH$_2$CH$_2$;

a is a number of 0 to 6 with the proviso that the average value of subscript a for the product is greater than zero and such that a significant amount, e.g. at least about 20 percent, of the hydroxyl groups in the product are primary; and m is a number of 1 to 6.

Subclasses of the hydroxyl-terminated poly(glycidyl azide) products described above are those represented by one of the general formulas:

  G'[(E')$_n$(R$^1$CH$_2$O)$_a$H]$_m$  VII-1

  G'[(E')$_n$R$^{2'}$CH$_2$OH]$_m$  VII-2

  HOCH$_2$R$^{3'}$O(E')$_n$H  VIII

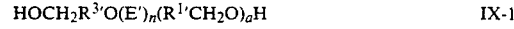  HOCH$_2$R$^{3'}$O(E')$_n$(R$^{1'}$CH$_2$O)$_a$H  IX-1

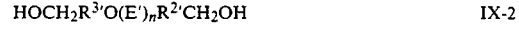  HOCH$_2$R$^{3'}$O(E')$_n$R$^{2'}$CH$_2$OH  IX-2

  [HOCH$_2$R$^{3'}$O(E')$_n$]$_p$Z$^1$  X-1

  [HOCH$_2$R$^{3'}$O(E')$_n$]$_p$Z$^2$  X-2 where, in the above formulas (E')$_n$, n, a, and m are as defined for formula VI;

G' is an oxygen atom or the residue of an organic polyhydroxyl compound (such as the active hydrogen-free residue of an initiator for the polymerization of epichlorohydrin), e.g., —OCH$_2$CH$_2$O—, —O(CH$_2$)$_3$O—, —O(CH$_2$)$_4$O—, —OCH$_2$C$_6$H$_{10}$CH$_2$O—, —OCH$_2$CH(CH$_2$N$_3$)O—, CH$_3$CH$_2$C(CH$_2$O+$_3$, —OCH$_2$CH(CH$_3$)O—, C(CH$_2$O+$_4$, —OC$_6$H$_{10}$O—;

R$^{1'}$ is a divalent organic group such as aliphatic group having 1 to 10 carbon atoms (such as derived from a cyclic chain extender reacted with a hydroxyl group of a polyepichlorohydrin), e.g., $-(CH_2)_b-$, $-CO(CH_2)_b-$, $-CH_2C(CH_3)_2-$, $-CH_2(CH_2N_3)_2-$, and $-CH_2CH_2OCH_2-$, where b is a number of 1 to 6, R$^{2'}$ is a divalent organic group such as aliphatic group having 1 to 10 carbon atoms (such as that derived from a blocked chain extending reagent), e.g., $-(CH_2)_b-$, $-CO(CH_2)_b-$, $-CH_2C(CH_3)_2-$, $-CH_2CH(CH_3)-$, $-CONH(CH_2)_b-$, $-CH_2C_6H_4-$ and $-CH_2C_6H_{10}-$, and b is as defined above;

R$^{3'}$ a divalent organic group such as aliphatic group having 1 to 10 carbon atoms (such as derived from a blocked initiator) which is stable under epichlorohydrin polymerization conditions, e.g., $-(CH_2)_b-$, $-CH(CH_2N_3)-$, $-C(CH_3)_2-$, $-CO-$, $-(CH_2)_bCO-$, $-C(CH_2N_3)_2CH_2-$, $-C(CH_3)_2CH_2-$, $-CH(CH_3)-$, $-CH_2OCH_2(CH_2)_b-$, and b is as defined above;

p is a number equal to the valence of $Z^1$ or $Z^2$, which valence is 1 to 6; and $Z^1$ and $Z^2$ are as defined above for $Z^1$ and $Z^2$, respectively, for formulas V-1 and V-2.

It is also within the scope of this invention to convert secondary hydroxyl terminated poly(glycidyl azide) to primary hydroxyl terminated polyglycidyl azide) utilizing the types of reagents employed in Schemes II-1 and II-2. Another process within the scope of this invention would use the azide ion as an unblocking reagent in Schemes II-2, III, IV-1, IV-2, V-1, or V-2 while also accomplishing the transformation of the polyepichlorohydrin products of this invention to the poly(glycidyl azide) products of this invention.

The poly(glycidyl azide) products of this invention, by virtue of their faster-reacting primary-hydroxyl functionality, are much less susceptible to undesired side reactions during cure with isocyanates under urethane bond-forming conditions. One such undesired side reaction is that of isocyanate with adventitious moisture or water. Water reacts with isocyanate to form a urea linkage and liberates carbon dioxide, a by-product which is highly deleterious in energetic compositions since it can produce bubbles (or "voids") which decrease the density of such compositions and may change the burning rate thereof. Loss of isocyanate to this side reaction also changes the stoichiometric ratio (NCO/OH) of isocyanate-to-hydroxyl groups and provides an elastomer of inferior mechanical properties. Another undesired side reaction which can take place is oxidation of the secondary hydroxyl groups by oxidizer components of the propellant compositions. The ketonic products of such oxidation are unreactive with isocyanate and therefore ineffective as chain-extending or crosslinking groups. The formation of biuret linkages by reaction of isocyanate with urethane moieties is another undesired side reaction which can occur if the hydroxyl-isocyanate reaction is slow, as in the case of secondary hydroxyl groups.

In using the poly(glycidylazide) polymer products as binder prepolymers for solid rocket propellants, they can be mixed with an optional liquid plasticizer and then with solid particulate oxidizer, optionally other fuel components, bonding agents, processing aids, burn rate catalysts, cure catalysts, carbon black, and combustion stabilizers. These propellant ingredients can be blended in a slow speed, high-shear mixer until all the solid particles are wetted by the liquids in the system, the mixing optionally being carried out under vacuum to remove trapped air. A polyisocyanate curing agent is then added. An additional short mixing cycle is completed. The viscous, uncured propellant slurry can be transferred into a prepared rocket motor casing. The filled casing can then be slowly heated to the appropriate cure temperature (generally 55° to 80° C.) and held at that temperature until the urethane reaction has taken place and the liquid binder precursor is converted to a solid, elastomeric polyurethane matrix providing mechanical integrity, environmental protection, and a controlled burning surface to the resulting solid propellant. Such propellants can be used in aircraft starter cartridges and ducted rocket boosters, and, as high energy propellant, low signature propellants, minimum smoke propellant, and gun propellants.

Further details on preparation of the above-described polyurethanes and their use as binders for solid rocket propellants will be omitted in the interest of brevity, since the steps in preparing such polyurethanes and propellants are well-known, e.g, see U.S. Pat. Nos. 3,642,705 (Zollinger) and 4,379,903 (Reed et al.) and "Rocket Propulsion Elements", G. P. Sutton et al, John Wiley & Sons, New York, 4th Ed. Chap. 11 (1976) whose disclosures are incorporated herein by reference for such purpose.

The hydroxyl-terminated poly(glycidyl azide) polymer products of this invention can also be used as energetic binders for explosive compositions, particularly where the latter are used in weight- or volume-limited applications in which conventional binders are not sufficiently energetic.

The glycidyl azide polymers can also be converted to polyurethanes or polyesters in the same way described above for the preparation of polyurethanes and polyesters from the hydroxyl-terminated polyepichlorohydrin products of this invention. The polyurethanes, polyesters, or precursor reaction mixtures thereof, prepared from the poly(glycidyl azide) polymers, as described above, can also be used as fugitive binders for binding or aggregating sand or other particulates used, for example, in making fusible plugs, foundry molds and cores, etc. Such fugitive binders will have good mechanical properties over a temperature range of $-50°$ to 120° C., but advantageously can be decomposed at a relatively low temperature, e.g., below 130°-150° C. The polyurethanes, polyesters, or precursor mixtures thereof, can also be used as temporary protective or masking coatings or primer therefor, e.g, on plastic substrates such as polyester film, which coatings can be removed by low temperature thermal treatment or ultra-violet radiation.

The polyurethanes or polyesters, or precursor reaction mixtures thereof, can also be used as adhesives for joining materials which thereafter can be separated by thermal treatment or ultra-violet treatment in the case of transparent articles, to remove the adhesive by its decomposition. Heat decomposible films can be made of such polyurethanes or polyester, such films being used as carriers or as temporary electrical insulators or gas-generating sources. The polyurethane or polyester can be formed in spherical shape by suspension curing the precursor mixtures thereof in an immiscible fluid, and the spherical articles thus prepared used as gas-generating beads or powder or coated with an elastomeric coating, the thermal treatment or ultra-violet irradiation of such articles producing gas-filled spheres or balloons and thus lightweight or low density articles. The polyurethanes or polyesters can be used as imageable coatings, the image being developed by thermal treatment or ultra-violet irradiation. Foams made from such polyurethanes or polyesters can be used as temporary or fugitive thermal insulation.

Objects and advantages of this invention are illustrated in the following examples.

EXAMPLE 1

To a 2-L, 3-necked flask, equipped with an electric heating mantle, stirrer, thermometer, condenser, addition funnel and gas inlet tube, were added 100 g 1,2-dichloroethane solvent and 72.1 g 1,4-bis(hydroxymethyl)cyclohexane initiator. A slow, dry nitrogen gas purge was started and maintained throughout the reaction and solvent stripping operation. To the well-stirred solution heated to 65° C. was added, by means of a syringe, 7.5 g stannic chloride. The heating source was removed and 928 g epichlorohydrin was added with stirring over a one-hour period while maintaining the reaction temperatures at 65 to 70° C. for an additional 22 hours. To the stirred solution of the resulting secondary hydroxyl-terminated polyepichlorohydrin (containing active tin catalyst from the polymerization reaction) was added an additional 4.4 g $SnCl_4$ catalyst in 50 g 1,2-dichloroethane, then 88 g of ethylene oxide gas was added over a period of eight hours by bubbling the gas into the solution, using a dry ice-cooled condenser. The mixture was stirred for an additional 16 hours at 65° C. and then solvents and volatile materials were removed at about 65° C. under reduced pressures (5 torr) over a five-hour period.

To remove the catalyst from the crude, chain-extended polyepichlorohydrin product, it was diluted with 100 g 1,2-dichloroethane, and 500 g of a 10% aqueous methanol solution containing 22 g of ethylenedinitrilotetraacetic acid, tetrasodium salt, was added, and the mixture stirred vigorously for two hours at 65° C. The two liquid phases were allowed to separate at room temperature and the lower phase extracted with 500 g 10% aqueous methanol at 65° C. The phases were separated as before at room temperature and the lower phase extracted again with 500 g of 10% aqueous methanol at 65° C. The lower phase, which separated at room temperature, was stripped of solvent and volatiles at 5 torr over a six-hour period to yield purified, liquid polyepichlorohydrin diol having the following structure which falls within formula II-1:

$$H(OCH_2CH_2)_a(OCHCH_2)_nOCH_2C_6H_{10}CH_2O(CH_2CHO)_n(CH_2CH_2O)_aH$$
$$\qquad\qquad\quad | \qquad\qquad\qquad\qquad\qquad\qquad\qquad |$$
$$\qquad\qquad\quad CH_2Cl \qquad\qquad\qquad\qquad\qquad\qquad CH_2Cl$$

The product had a viscosity of 92,800 centipoise at 22° C. Proton nmr analysis (at 270 MHz) showed the presence of 34% primary and 66% secondary hydroxyl groups.

EXAMPLE 2

To 22.8 g (0.2 mole) of trifluoroacetic acid stirred in an ice-cooled flask was added 102 grams (1.1 moles) of epichlorohydrin at such a rate as to maintain the reaction temperature at 60°-70° C. Excess epichlorohydrin was removed under reduced pressure (35 torr) to yield the initiator $CF_3CO_2CH_2CH(CH_2Cl)OH$ product which contained some isomeric $CF_3CO_2CH(CH_2Cl)C-H_2OH$. $SnCl_4$ catalyst (3.1 g) was added. The temperature was held at 70°-75° C. while an additional 275 g epichlorohydrin was added over a 90-minute period. The reaction mixture was stirred an additional 16 hours at 70° C., stripped at 70° C. and 5 torr for two hours. The stripped, blocked polyepichlorohydrin intermediate was unblocked by reacting it with a mixture of 180 g methanol, 20 g water, and 20 g concentrated ammonium hydroxide, first at a temperature of 30° C. for 30 minutes and then at 65° C. for 90 minutes. The pH of the aqueous phase was neutral (about 7). The organic phase was washed twice with a solution of 180 g of methanol and 20 g of water, then stripped at 60° C. at 5 torr to yield the desired primary hydroxyl-terminated polyepichlorohydrin polyol, having a structure like that of formula III, supra, Scheme III, where $R^3$ is $—CH(CH_2Cl)—$. Proton nmr analysis at 100 MHz showed the presence of 19% primary and 81% secondary hydroxyl groups.

EXAMPLE 3

To 114 g (1.0 mole) trifluoroacetic acid in a 500 ml flask was added 44 g (1.0 mole) ethylene oxide gas while stirring. The temperature was allowed to rise to 40° C. where it was maintained by adjusting the rate of addition of the gas and cooling with a water-ice bath. The addition of gas took 55 minutes. After an additional 60 minutes of stirring, while the flask cooled to room temperature, the flask contents (154 g) were transferred to a 5 L flask and 15 g of $SnCl_4$ added. The flask was heated to 65° C. and with vigorous stirring a slow addition of 1842 g of epichlorohydrin was begun. The temperature was maintained between 65° C. and 70° C. by adjusting the rate of addition and cooling with a water-/ice bath. After about 2 hours of reaction, 250 g of 1,2-dichloroethane was added to help moderate the vigorous reaction. The reaction mixture was allowed to stir at 65° C. for an additional 18 hours. At this point, another 44 g (1 mole) of ethylene oxide was added while maintaining the temperature at 65° C. by addition rate adjustment and cooling. After completing the addition, the reaction mixture was allowed to stir at 65° C. for another 1½ hours, then cooled to 30° C. The resulting blocked, chain-extended polyepichlorohydrin reaction product (mainly a polymer having a structure like that of formula M of Scheme IV-1, supra, where $R^1$ and $R^2$ are both $—CH_2—$), was unblocked by reacting with a solution prepared from 30 g ethylenedinitrilotetraacetic acid, tetrasodium salt, in 100 g water, 900 g methanol, and 56 g 18% aqueous $NH_4OH$. After 1 hour 20 minutes of vigorous stirring, the mixture was heated to 65° C. before transferring to separatory funnels. The lower phase was returned to the flask and washed twice with 1000 g of 10% aqueous methanol, then stripped at 65°-70° C. at 5 torr to yield the final product, within the scope of formula IV-1, having the structure:

$$HOCH_2CH_2O(CH_2CHO)_n(CH_2CH_2O)_aH$$
$$\qquad\qquad\quad |$$
$$\qquad\qquad\quad CH_2Cl$$

and a hydroxyl equivalent weight of 1560 and 40% primary and 60% secondary hydroxyl groups as determined by proton nmr at 270 MHz.

EXAMPLE 4

The procedure, reagents, and amounts used for Example 3 above were used in this example, except that only 7.5 g of the SnCl$_4$ catalyst was employed (50% of that used in Example 3). The resulting hydroxyl-terminated polyepichlorohydrin had a hydroxyl equivalent weight of 1,220 (phenyl isocyanate titration), with 37% primary and 63% secondary hydroxyl terminal groups as determined by proton nmr at 270 MHz.

EXAMPLE 5

An initiator solution was prepared by the addition of 57 g (1.30 moles) of ethylene oxide to a solution of 144 g (1.26 moles) of trifluoroacetic acid in 200 g 1,2-dichloroethane at 20°–30° C. to form a solution containing the resulting CF$_3$COOCH$_2$CH$_2$OH initiator, with some CF$_3$COOCH$_2$CH$_2$OOCCF$_3$, HOCH$_2$CH$_2$OH, and small amounts of oligomers also present in the solution, as shown by proton nmr analysis. Catalyst, 0.44 g SnCl$_4$, about 25% of the relative amount used in Example 3, was added to 10% of the above initiator solution (0.125 mole) in a reaction flask. Epichlorohydrin (184.5 g, 2.0 moles) was then added over a one-hour period at 65°–70° C., and heating continued for one hour. The reaction mixture was cooled to about 20° C., then extracted and worked up as described in Example 3. The resulting primary hydroxyl-terminated polyepichlorohydrin product had a hydroxyl equivalent weight of 1,160, with 25% primary and 75% secondary hydroxyl terminal groups (proton nmr at 270 MHz), and a structure corresponding to that of general formula III where R$^3$ is CH$_2$.

EXAMPLE 6

An initiator solution was prepared in 50 g of 1,2-dichloroethane solvent from 11 g (0.25 mole) ethylene oxide and 40.9 g (0.25 mole) trichloroacetic acid, following the procedure described in Example 5, to yield a solution containing the resulting initiator CCl$_3$COOCH$_2$CH$_2$OH along with by-products as described in Example 5.

Catalyst, 0.44 g SnCl$_4$, was added to 40% (0.1 mole) of the above initiator solution in a reaction flask, and 184.5 g (2.0 moles) of epichlorohydrin added over a 40 minute period, the reaction temperature being maintained at 65°–68° C. with cooling as needed. The reaction mixture was allowed to cool to about 30° C., then extracted and worked up as described in Example 3. The resulting hydroxyl-terminated polyepichlorohydrin product had a hydroxyl equivalent weight of 1.190 with 31% primary hydroxyl and 69% secondary hydroxyl groups (proton nmr at 270 MHz) and a structure corresponding to formula III where R$^2$ is CH$_2$.

EXAMPLE 7

100 g of the polyepichlorohydrin polyol product of Example 1, dissolved in 100 g of dimethyl sulfoxide, was added to a stirred slurry of 100 g of sodium azide in 230 g of dimethylsulfoxide. The mixture was heated to 80° C. and maintained at that temperature for 24 hours and the supernatant liquid was decanted from the precipitated salts into an equal volume of cold water. The water-diluted supernatant liquid was heated to 80° C. and stirred for two hours, the phases allowed to separate, the aqueous phase discarded, and the water washing repeated twice more. Then 120 g of 1,2-dichloroethane was added to the organic phase and the solution was washed three times with 600 g portions of water. The separated organic phase was stripped at 40°–45° C. and 5 torr with a slow N$_2$ purge for 6 hours, to yield a glycidyl azide polymer product having the following structure within the scope of formula VII-1:

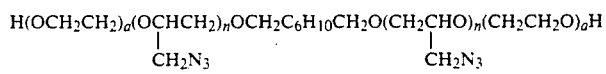

EXAMPLES 8, 9, 10, 11

In these examples, primary hydroxyl group-containing polyepichlorohydrin polyol ("PECH") products of this invention and glycidyl azide derivatives thereof ("GAP") were reacted and gelled with polyisocyanate, "DESMODUR" N-100, catalyzed by dibutyltin dilaurate, to form elastomeric polyurethane products.

As comparative examples (C-1, C-2), polyepichlorohydrin polyol and a glycidyl azide derivative thereof, terminated with secondary hydroxyl groups only, were also gelled with the same reagents. In all runs, the polyols were mixed at room temperature with 2 g of the isocyanate, and the indicated amount of catalyst and the time to gel was noted.

The runs and results are shown in Table 1. Note that the primary hydroxyl-containing polyols gelled faster than the secondary hydroxyl-containing polyols.

TABLE I

| Ex. No. | Polymer used | Hydroxyl type | Source of polymer used | Amt. of polyol, g | Drops of tin catalyst | Time to gel (25° C.), minutes |
|---|---|---|---|---|---|---|
| 8 | PECH[a] | primary | Ex. 1 | 10.6 | 1 | 34 |
| 9 | PECH | primary | Ex. 2 | 10.0 | 1 | 24 |
| C-1 | PECH | secondary | [c] | 10.6 | 1 | 52 |
| 10 | GAP[b] | primary | Ex. 7 | 11.0 | 4 | 82 |
| C-2 | GAP | secondary | [d] | 11.0 | 4 | 137 |
| 11 | PECH | primary | Ex. 3 | 10.6 | 1 | 23 |

[a]"PECH" means hydroxyl-terminated polyepichlorohydrin.
[b]"GAP" means hydroxyl-terminated poly(glycidyl azide) polymer.
[c]PECH used was prepared following procedure of Example 1 except that ethylene oxide addition was not done.
[d]Polymer used was prepared from PECH described in footnote c using procedure of Example 7.

Various modifications and alterations of this invention will be apparent to those skilled in the art without departing from the scope and spirit of this invention,

What is claimed is:

1. A normally liquid, hydroxyl-terminated poly(glycidyl azide) product comprising polymer having poly(glycidyl azide) homopolymer chains, which make up the major portion of the product by weight, at least about 20 percent of said chains terminating in a moiety containing a single hydroxyl group which is a primary hydroxyl group, wherein said polymer is represented by one of the general formulas:

| | |
|---|---|
| $G'[(E')_n(R1'CH_2O_aH]_m$ | VII-1 |
| $G'[(E')_nR2'CH_2OH]_m$ | VII-2 |
| $HOCH_2R3'O(E')_nH$ | VIII |
| $HOCH_2R3'O(E')_n(R1'CH_2O)_aH$ | IX-1 |
| $HOCH_2R3'O(E')_nR2'CH_2OH$ | IX-2 |
| $[HOCH_2R3'O(E')_n]_pZ^1$ | X-1 |
| $[HOCH_2R3'O(E')_n]_pZ^2$ | X-2 | where, in the above formulas:
n is a number greater than 1;
E' is an azidomethylethyleneoxy unit;
$(E')_n$ is a poly(glycidyl azide) chain;
a is a number of 0 to 6 with the proviso that the average value of subscript a for the product is greater than zero and such that at least about 20 percent of the hydroxyl groups in the product are primary;
m is a number of 1 to 6;
G' is an oxygen atom or the residue of an organic polyhydroxyl compound;
R1' is a divalent organic group;
R2' is a divalent organic group;
R3' is a divalent organic group;
p is a number equal to the valence of $Z^1$ and $Z^2$, which valence is 1 to 6;
$Z^1$ is a linking group which is the residue of a hydroxyl-reactive reagent; and
$Z_2$ is the group formed from a linking reagent which reacts with hydroxyl groups by an addition process.

2. A normally-liquid hydroxyl-terminated poly(glycidyl azide) product according to claim 1 comprising polymer having the following general structure:

$$H(OCH_2CH_2)_a(OCHCH_2)_nOCH_2C_6H_{10}CH_2O(CH_2CHO)_n(CH_2CH_2O)_aH$$
$$\qquad\qquad\qquad\; |\qquad\qquad\qquad\qquad\qquad\qquad |$$
$$\qquad\qquad\qquad CH_2N_3\qquad\qquad\qquad\qquad\qquad CH_2N_3$$

where, in the above formula, n and a are as defined in claim 1.

3. A normally liquid, hydroxyl-terminated poly(glycidyl azide) product according to claim 1 wherein said polymer is represented by the general formula $$G'[(E')_n(R1'CH_2O)_aH]$$

wherein G', E', n, R1' and a are as defined in claim 1.

4. A normally liquid, hydroxyl-terminated poly(glycidyl azide) product according to claim 1 wherein said polymer is represented by the general formula $$G'[(E')_nR2'CH_2OH]_m$$

wherein G', E', n, R2' and m are as defined in claim 1.

5. A normally liquid, hydroxyl-terminated poly(glycidyl azide) product according to claim 1 wherein said polymer is represented by the general formula $$HOCH_2R3'O(E')_nH$$

wherein R3', E' and n are as defined in claim 1.

6. A normally liquid, hydroxyl-terminated poly(glycidyl azide) product according to claim 1 wherein said polymer is represented by the general formula $$HOCH_2R3'O(E')_n(R1'CH_2O)_aH$$

wherein R3', E', n, R1' and a are as defined in claim 1.

7. A normally liquid, hydroxyl-terminated poly(glycidyl azide) product according to claim 1 wherein said polymer is represented by the general formula $$HOCH_2R3'O(E')_nR2'CH_2OH$$

wherein R3', E', n and R2' are as defined in claim 1.

8. A normally liquid, hydroxyl-terminated poly(glycidyl azide) product according to claim 1 wherein said polymer is represented by the general formula $$[HOCH_2R3'O(E')_n]_pZ^1$$

wherein R3', E', n, p and $Z^1$ are as defined in claim 1.

9. A normally liquid, hydroxyl-terminated poly(glycidyl azide) product according to claim 1 wherein said polymer is represented by the general formula $$[HOCH_2R3'O(E')_n]_pZ^2$$

wherein R3', E', n, p and $Z^2$ are as defined in claim 1.

* * * * *

UNITED STATES PATENT AND TRADEMARK OFFICE
CERTIFICATE OF CORRECTION

PATENT NO. : 5,164,521

DATED : Nov. 17, 1992

INVENTOR(S) : Manzara et al.

It is certified that error appears in the above-indentified patent and that said Letters Patent is hereby corrected as shown below:

Col. 1, line 38, "0 042 505 A3 A" should be
--0 042 505 A3--.

Col. 2 line 38, "$(RCH_2O),H$" should be --$(RCH_2O)_zH$--.

Col. 3, line 33, "subscript greater" should be --subscript a for the product is greater--.

Col. 4, line 1, "$-CH_2\!\!\not\,\,_b$" should be --$\!\!-\!\!(CH_2\!\!\not\,\,_b$--.

Col 5, line 43, "$[(E_nH]_m + maR^1$" should be --"$[(E)_nH]_m + m\ aR^1$--.

Col. 6, line 21, "2 D" should be --2. D--.

Col. 7, line 23, "d®scribed" should be --described--.

Col. 7, line 49, "in IV-2." should be --in connection with Scheme II-2 to yield the product of formula IV-2.--.

Col. 14, line 35, "$CH_2$;" should be --$CH_2-$;--.

UNITED STATES PATENT AND TRADEMARK OFFICE
CERTIFICATE OF CORRECTION

PATENT NO. : 5,164,521

DATED : Nov. 17, 1992

INVENTOR(S) : Manzara et al.

It is certified that error appears in the above-indentified patent and that said Letters Patent is hereby corrected as shown below:

Col. 15, line 12, "2--b," should be --$2\!\!+\!\!_b$,--.

Col. 15, line 22, "$H_2$--b," should be -- $H_2\!\!+\!\!_b$,--.

Col. 15, line 29, "polyglycidyl" should be --poly(glycidyl--.

Col. 18, line 49, "18% aqueous" should be --28% aqueous--.

Col. 21, line 14, "$G'[(E')_n(R1'CH_2O_aH]_m$"
should be -- $G'[(E')_n(R1'CH_2O_aH)]_m$--.

Signed and Sealed this

Twenty-seventh Day of February, 1996

Attest:

BRUCE LEHMAN

Attesting Officer

Commissioner of Patents and Trademarks